(12) United States Patent
De Vries et al.

(10) Patent No.: US 11,363,949 B2
(45) Date of Patent: Jun. 21, 2022

(54) EYE MEASURING APPARATUS

(71) Applicant: Cassini Technologies B.V., 's-Gravenhage (NL)

(72) Inventors: Haaije Rimmer De Vries, 's-Gravenhage (NL); Roland Bryn Piper, 's-Gravenhage (NL)

(73) Assignee: Cassini Technologies B.V., 's-Gravenhage (NL)

( * ) Notice: Subject to any disclaimer, the term of this patent is extended or adjusted under 35 U.S.C. 154(b) by 50 days.

(21) Appl. No.: 16/495,875

(22) PCT Filed: Apr. 13, 2018

(86) PCT No.: PCT/NL2018/050231
§ 371 (c)(1),
(2) Date: Sep. 20, 2019

(87) PCT Pub. No.: WO2018/190717
PCT Pub. Date: Oct. 18, 2018

(65) Prior Publication Data
US 2020/0008669 A1 Jan. 9, 2020

(30) Foreign Application Priority Data
Apr. 13, 2017 (NL) ...................... 2018712

(51) Int. Cl.
*A61B 3/107* (2006.01)
*A61B 3/117* (2006.01)
*A61B 3/14* (2006.01)

(52) U.S. Cl.
CPC .............. *A61B 3/107* (2013.01); *A61B 3/117* (2013.01); *A61B 3/14* (2013.01)

(58) Field of Classification Search
CPC ............ A61B 3/107; A61B 3/117; A61B 3/14
(Continued)

(56) References Cited

U.S. PATENT DOCUMENTS

| 4,902,123 A | 2/1990 | Yoder, Jr. |
| 6,692,126 B1 | 2/2004 | Xie et al. |

(Continued)

FOREIGN PATENT DOCUMENTS

| JP | H3-66356 A | 3/1991 |
| JP | H10-500033 A | 1/1998 |

(Continued)

OTHER PUBLICATIONS

Japanese Application No. 2019-554413, Office Action dated Jan. 18, 2022, 8 pages.

*Primary Examiner* — Mohammed A Hasan
(74) *Attorney, Agent, or Firm* — Hoffmann & Baron, LLP

(57) ABSTRACT

An eye measuring apparatus includes a stimulator including multiple stimulator light points for projecting a plurality of light rays onto a surface of the cornea of an eye; a camera system for capturing reflected images of the stimulator light points; and a computational unit arranged to analyse the posterior surface of the cornea and/or to obtain a characteristic of the eye on the basis of the reflected images. The control unit is arranged to activate subsequently different subsets of the multiple stimulator light points; and to carry out the following steps: selecting, for each of the different subsets of the multiple stimulator light points, at least one reflected image that corresponds with activation of the respective subset of the multiple stimulator light points, and combining the selected reflected images with each other to analyse the posterior surface of the cornea and/or to obtain the characteristic of the eye.

24 Claims, 6 Drawing Sheets

(58) Field of Classification Search
USPC .......................................................... 351/212
See application file for complete search history.

(56) References Cited

U.S. PATENT DOCUMENTS

| | | | |
|---|---|---|---|
| 2013/0093998 A1* | 4/2013 | Bishop ................... | G02C 7/047 |
| | | | 351/208 |
| 2014/0340637 A1* | 11/2014 | Trumm .................... | G02C 7/06 |
| | | | 351/206 |
| 2015/0138505 A1* | 5/2015 | Grenon ................ | A61B 3/0008 |
| | | | 351/206 |
| 2015/0150448 A1 | 6/2015 | Takii et al. | |
| 2015/0238078 A1 | 8/2015 | Ebersbach et al. | |
| 2016/0220113 A1* | 8/2016 | Frey ..................... | A61B 3/1025 |

FOREIGN PATENT DOCUMENTS

| | | | |
|---|---|---|---|
| JP | 2005-102938 A | 4/2005 | |
| JP | 2012-217567 A | 11/2012 | |
| JP | 2015-104554 A | 6/2015 | |
| JP | 2015-531276 A | 12/2015 | |
| JP | 2017-47129 A | 3/2017 | |
| WO | 95/22925 A1 | 8/1995 | |
| WO | 2009/127442 A1 | 10/2009 | |

* cited by examiner

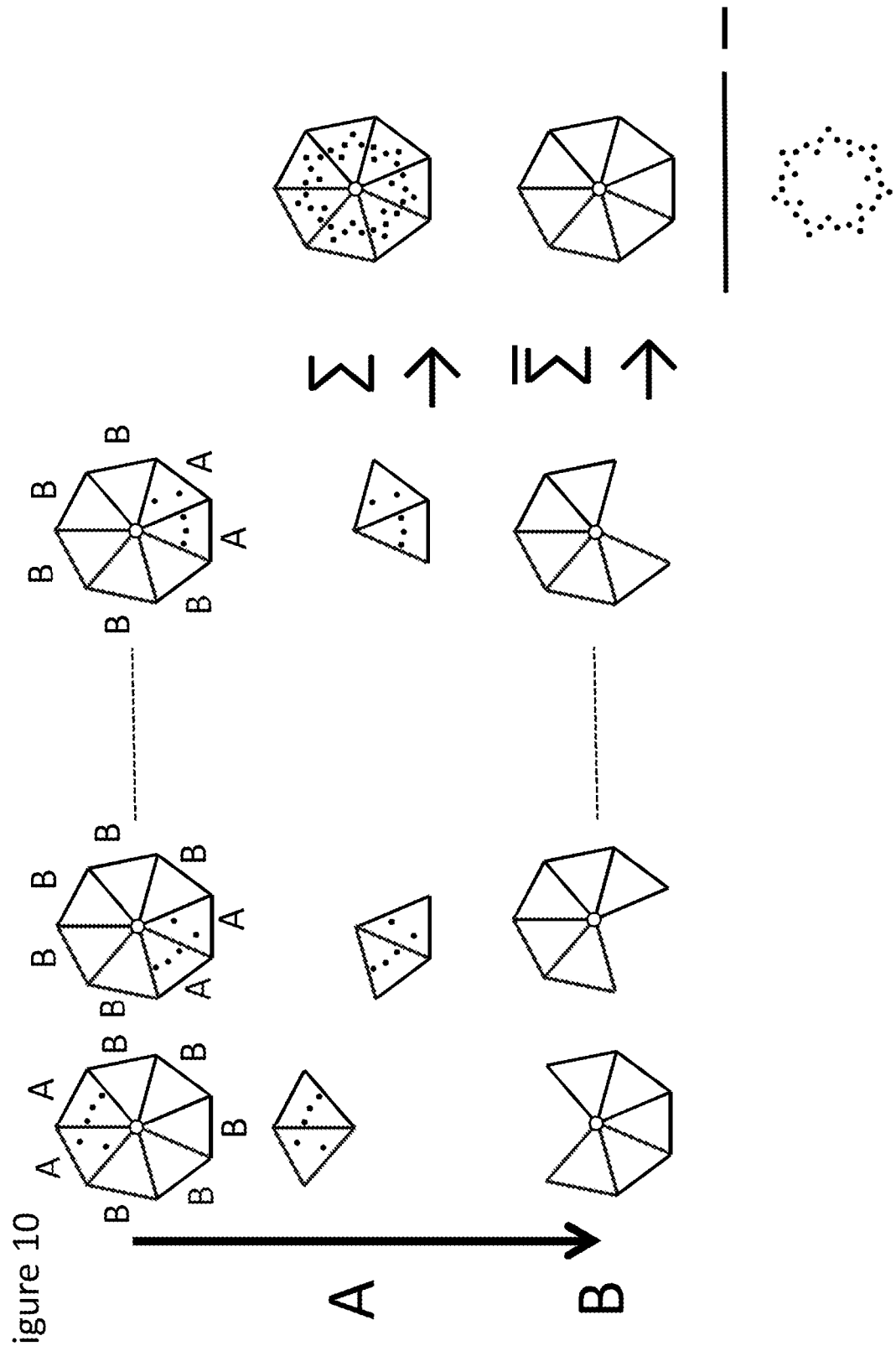

EYE MEASURING APPARATUS

CROSS-REFERENCE TO RELATED APPLICATIONS

This application is the National Stage of International Application No. PCT/NL2018/050231, filed Apr. 13, 2018, which claims the benefit of Netherlands Application No. 2018712, filed Apr. 13, 2017, the contents of which is incorporated by reference herein.

FIELD OF THE INVENTION

The present invention relates to an eye measuring apparatus and a method for measuring a cornea of an eye.

BACKGROUND OF THE INVENTION

A method and apparatus for determining a corneal thickness of an eye is known from U.S. Pat. No. 6,692,126. The apparatus disclosed applies a Placido ring illuminator to illuminate the cornea and derives a model of the anterior surface of the cornea from the image obtained. By projecting thin slits of light on the cornea, a second image can be taken and used to determine the corneal thickness from the model of the anterior surface and the second image. The apparatus and method as known in the art suffers from a number of drawbacks. First of all, this system needs to focus on two different planes: firstly the iris plane for imaging the reflections of the Placido illuminator, and secondly the cornea plane for imaging the cornea, which is partially illuminated by the slits of light. It is known that the use of a Placido ring illuminator requires some assumptions with respect to the corneal anterior surface. Due to the use of ring shaped light sources, a one-to-one correspondence between a point on the stimulator source (i.e. the Placido ring illuminator) and a point on the captured image cannot be determined unless certain symmetries in the corneal surface are assumed. As in reality, these assumed symmetries may not be present; inaccuracies may be introduced in the model. As the model is further on applied to determine the corneal thickness, inaccuracies in this thickness due to the assumed symmetries of the anterior surface may occur as well. It can further be noted that the use of slit-shaped illumination sources results in a similar problem in that a one to one correspondence between a point on the stimulator source (i.e. the slit-shaped illumination source) and a point on the captured image may be difficult to establish. A further drawback of the apparatus as known in the art is the requirement of sequentially capturing two images of the cornea to determine the corneal thickness. In case of a displacement of the eye between the capturing of the first and the second image, some uncertainty with respect to the position of the anterior surface of the cornea may exist when the second image is taken. This uncertainty may further introduce inaccuracies in the determination of the corneal thickness. As an alternative, it is proposed in U.S. Pat. No. 6,692,126 to use a camera system with multiple camera's each camera being arranged to record an image of one of the illumination sources. This may result in a more complex and therefore more expensive apparatus.

An improved method for determining the corneal thickness of an eye is disclosed in WO 2009/127442, the contents of which are herein incorporated by reference, in its entirety. This method comprises the following steps:
illuminating a cornea by a plurality of stimulator point light sources,
capturing an image of the cornea comprising reflected images of the stimulator point light sources,
obtaining a model representing an anterior surface of the cornea,
constructing a second model representing a posterior surface of the cornea from the image by ray-tracing the reflected images of the stimulator point light sources towards the model representing the anterior surface of the cornea,
determining the corneal thickness from the model representing the anterior surface and the second model representing the posterior surface.

According to an embodiment of this method, a first image is used to obtain a model of the anterior surface of the cornea and a second image is used for constructing the second model representing the posterior surface of the cornea. As the brightness of the direct reflection of the anterior surface and the direct reflection of the posterior surface of the cornea is substantially different, for example a factor 100, this way of determining a model for the posterior surface allows to use different illumination levels of the stimulator light points for imaging the anterior surface and for imaging the posterior surface of the cornea. Furthermore, the use of a first image for the anterior surface and a second image for the posterior surface provides a further advantage in that the camera system of the apparatus can set such that for each of the two images a different focus used. In this respect, it can be noted that the anterior surface and the posterior surface of the cornea are not in the same plane and as such, an image of the cornea may not have the anterior surface and the posterior surface in focus.

However, the construction of a model of the posterior surface of the cornea remains a challenge. Only a limited part of the light emitted from the stimulator light points will be reflected by the posterior surface of the cornea and directly return to the camera system, i.e. the direct reflection, while much of the light of the stimulator light points will be reflected by other surfaces such as the anterior cornea surface and the posterior lens surface, or will be absorbed by the tissue of the eye. Therefore, there is a desire to increase the illumination level of the stimulator light points to obtain a more clear image of the reflections originating on the posterior surface of the cornea. But this would also result in an increase in reflections from unwanted sources such as iris, cataract, eyelashes, etc. . . . . Each of these has a negative effect on the clarity of the reflections that originate on the posterior surface of the cornea.

SUMMARY OF THE INVENTION

The aim of the present invention is to provide an improved eye measuring apparatus and method for measuring the cornea of the eye, or at least to provide an alternative eye measuring apparatus and/or method.

The present invention provides an eye measuring apparatus, comprising:
a stimulator comprising multiple stimulator light points for projecting a plurality of light rays onto a surface of the cornea of an eye;
a camera system for capturing reflected images of the stimulator light points;
a computational unit arranged to analyse the posterior surface of the cornea and/or to obtain a characteristic of the eye on the basis of the reflected images; and
a control unit arranged to activate selectively one or more of the multiple stimulator light points, wherein the control unit is arranged to activate subsequently different subsets of the multiple stimulator light points, and wherein the computational unit is arranged to carry out the following steps:

selecting, for each of the different subsets of the multiple stimulator light points, at least one reflected image that corresponds with activation of the respective subset of the multiple stimulator light points, and combining the selected reflected images with each other to analyse the posterior surface of the cornea and/or to obtain the characteristic of the eye.

According to the invention, the posterior surface of the cornea is analysed on the basis of reflected images captured by the camera system, while subsequently activating different sub-sets of the multiple stimulator light points. From the captured reflected images, a number of reflected images is selected whereby, for each of the selected subsets of the multiple stimulator light points at least one reflected image is selected that corresponds with activation of the stimulator light point or points that belong to that subset.

The selected reflected images are combined with each other in order to analyse the posterior surface of the cornea, for example to analyse the shape of the posterior surface of the cornea or to construct a model of the posterior surface of the cornea. The use of different subsets of the multiple stimulator light points provides the possibility to improve the analysis of the posterior surface of the cornea, by activating a smaller number of stimulator light points for each image which enables the use of a higher illumination level for these stimulator light points. Since a smaller number of stimulator light points are illuminated at once, the background reflections are less present, and the resulting image is more suitable to determine relevant properties of the posterior surface of the cornea.

The subsets are selected such that all desired parts of the posterior surface are imaged in at least one of the selected reflected images. Further, the subsets are preferably selected such that the one or more stimulator light points of each subset are within a distinct sub-area of a stimulator projection area, i.e. a projection area of all stimulator light points of the stimulator, instead of distributed over the whole stimulator projection area.

The stimulator may comprise a conical or hemispherical stimulator projection surface comprising multiple stimulator light points for projecting a plurality of light rays onto a surface of the cornea of an eye. The conical or hemispherical stimulator projection surface is arranged around a center axis to be arranged coincident with the optical axis of the eye to be imaged. In such a stimulator, the one or more stimulator light points of each subset are arranged in an angular part of the stimulator projection surface. The angular part may for example extend over less than 180 degrees, preferably over less than 90 degrees of the circumference of the stimulator projection surface.

Each of the multiple stimulator light points may be part of its own subset. As an alternative, one or more of the multiple stimulator light points may be part of two or more subsets.

It is remarked that selecting the reflected images may comprise selecting all reflected images, for example when the frequency of capturing reflected images is the same as the frequency with which the control unit subsequently activated the different subsets of the multiple stimulator light points.

To obtain an image providing relevant information of the whole stimulator projection area, the selected reflected images may be combined into a combined image. This combined image may then be used to analyse the posterior surface of the cornea.

It is remarked, that, in an embodiment, each stimulator light point may have its own light source, for example a LED may be provided for each stimulator light point. In this embodiment the device will have a plurality of light sources. As an alternative, all stimulator light points of sub-sets of stimulator light points can be linked into a single light source, for example a light source of which light is distributed over multiple optical fibers, the end-points of the optical fiber forming stimulator light points to emit rays of light towards the cornea.

In an embodiment, the step of combining comprises separating, from each selected reflected image, a direct reflection area comprising a direct reflection of the one or more stimulator light points activated by the control unit, and combining the direct reflection areas of the selected reflected images into a single direct reflection image. Since it is known which subset of multiple light points is used for illumination of the cornea, it can be analysed in which area of the image the direct reflections from the posterior surface of the cornea may be expected. Since these direct reflections of the stimulator light points are in particular relevant for analysing the posterior surface of the cornea, for example to construct a model of the posterior surface of the cornea, these direct reflection areas may be separated from the rest of the image. By combining the direct reflection areas in a single direct reflection image, one image can be obtained which comprises relevant information with respect to the posterior surface of the cornea.

In an embodiment, the computational unit further is arranged to separate, from each selected reflected image, a background reflection area lacking a direct reflection of the one or more stimulator light points activated by the control unit, and combining the background reflection areas of the selected reflected images into a single background reflection image. By separating from each selected image a background reflection area, i.e. an area lacking direct reflections of the activated stimulator light points, and combining these background reflection areas into a single background reflection area, an image is obtained with information of the indirect reflections of the eye. These background reflections may for example comprise light that is scattered in the lens and/or reflected on the iris. This information may be useful to make a further assessment of the characteristics of the eye being examined.

In an embodiment, each selected reflected image is split in the direct reflection area and the background reflection area. This means that each part of a selected reflected image is either used as a direct reflection area or as a background reflection area.

In an embodiment, combining the background reflection areas of the selected reflected images into a single background reflection image comprises averaging the background reflection areas.

Each single background reflection image comprises a substantial part of the complete reflection image. In practice, the background reflection area may be substantially larger than the direct reflection area.

For example, the direct reflection area may correspond with an angular area of one seventh of the circumference of a substantial circular stimulator projection area, and the background reflection area may be the rest of the stimulator projection area, i.e. six sevenths of the stimulator projection area. When seven captured reflection images are selected with seven non-overlapping direct reflection areas, a complete single direct reflection image can be constructed by adding the seven direct reflection areas that are separated from the selected images into a single image. Correspondingly, seven background reflection areas can be separated, in particular the selected reflected image minus the direct reflection area. But, these background reflection areas each have a large overlap with each other of, in the above example, five sevenths of the stimulator projection area. Moreover, the background reflection areas are not directly illuminated, but are illuminated from a particular direction. To generate a representative background image information from all stimulator light points, other than those directly incident on each part of the cornea, should be combined. Therefore, the step of combining the background reflection areas into a single background reflection image preferably comprises averaging of the background reflection areas.

In an embodiment, combining the selected reflected images with each other comprises subtracting the single background reflection image from the single direct reflection image to obtain a background filtered single direct reflection image. The single direct reflection image comprises some background noise which is comparable with the background noise present in the single background reflection image. By subtracting the single background reflection image from the single direct reflection image, an image is obtained in which the background noise is filtered out. Such background filtered single direct reflection image is very useful for analysis of the posterior surface of the cornea of the eye, and possibly also for determining other characteristics of the eye.

It has also been found that the single background reflection image in itself may also be valuable to determine certain characteristics of the eye that is examined.

In an embodiment, the computational unit is arranged to determine on the basis of the single background reflection image a lens characteristic value representative for one or more lens characteristics of the eye. A substantial part of the background reflections is caused by direct and indirect reflections on the posterior surface of the lens of the eye. Typically, the direct reflections from the posterior lens surface appear, with respect to a center point of the image corresponding to a center axis of the stimulator, on the area of the reflected image diametrically opposed to the area where the direct reflections of the posterior surface of the cornea are found. Therefore, the background reflection image comprises direct reflections of the light rays emitted by the stimulator light points from the posterior lens surface. These direct reflections can be used to analyse the lens posterior surface.

Furthermore, the background reflection image comprises indirect reflections, for example caused by scattering of light in the lens of the eye.

The single background reflection image may therefore be used, in itself or with other measurements, to determine some characteristics of the lens, such as lens thickness, shape of the posterior surface of the lens, lens shape, lens tilt, decentration, etc.

In an embodiment, the computational unit is arranged to determine on the basis of the single background reflection image a value representative for the severity of cataract of the eye. A substantial part of the background reflections may be caused by light scattering of the light within the lens, in particular caused by cataract in the lens. The single background reflection image may therefore be used, in itself or with other measurements, to determine the state or progression of cataract in the lens, and may be used to assign a value relating to cataract severity to the lens. The single background reflection image may therefore be used to predict cataract at an early stage of its development.

In an embodiment, the control unit is arranged to activate simultaneously at least one stimulator light point of each respective subset of the multiple stimulator light points to obtain a further reflected image, wherein the computational unit is arranged to use the further reflected image to align the selected reflected images with respect to each other. The selected images are obtained from a series of captured images that are captured during subsequent activation of the subsets of the multiple stimulator light points. Thus some time is needed to capture all images taken during this subsequent activation. During this time, the eye may move with respect to the stimulator resulting in a positional shift between the captured reflected images.

In order to properly combine the direct reflection areas and/or the background reflection areas of the selected images into a single direct reflection image and/or background reflection image, respectively, it is of importance that the selected images are aligned with respect to each other. This alignment can be performed by using a further reflected image that is obtained during simultaneous activation of at least one stimulator light point of each subset of the multiple stimulator light points, so that the further reflected image comprises direct reflections of each subset. Preferably, the further reflected image comprises multiple direct reflections of each subset obtained by simultaneous activation of the multiple stimulator light points of each subset. Since the further reflected image comprises a direct positional relationship between the different subsets, the reflected images can be aligned with respect to each other on the basis of this further reflected image.

In an alternative embodiment, the subsets comprise common stimulator light points such that the selected reflected images can be aligned with respect to each other on the basis of the direct reflections of these common stimulator light points. The alignment of the selected images may also be carried out on the basis of other reference points, such as characteristics of the eye to be examined that are visible in all the selected reflected images.

In an embodiment, the control unit is arranged to adapt the illumination level of the multiple stimulator light points, and wherein the control unit is arranged to activate simultaneously the at least one stimulator light point of each respective subset of the multiple stimulator light points to obtain the further reflected image with a decreased illumination level compared with an illumination level used during the subsequent activation of the subsets of the multiple stimulator light points.

When a further reflected image is captured with activation of multiple stimulator light points, it may be desirable to decrease the illumination level of the multiple stimulator light points in order to avoid overexposure of the eye when capturing the further reflected image. For this reason the illumination level of the multiple stimulator light points may be adjustable by the control unit such that a suitable illumination level is selected when the further reflected image is taken.

In an embodiment, the stimulator comprising two or more stimulator segments, each stimulator segment comprising at least one stimulator light point, wherein each of the different subsets of the multiple stimulator light points is formed by one or more of the multiple stimulator light points of at least one of the two or more stimulator segments.

In practice, the stimulator may be formed by stimulator segments, in particular stimulator segment panels that are preferably arranged to form a conical or hemispherical shape. Each stimulator segment panel may for example be formed by a PCB.

Each stimulator segment comprises a stimulator surface comprising one or more stimulator light points. These stimulator light points of one segment may form one subset of the multiple stimulator light points. As a result, the subsets are non-overlapping and the number of subsets of the multiple stimulator light points corresponds to the number of stimulator segments.

In alternative embodiments, the stimulator light points of a part of a stimulator segment or the stimulator light points of multiple segments may form one subset of the multiple stimulator light points. These subsets may be overlapping or non-overlapping in the stimulator light points used for these subsets.

The stimulator segments may be wedge shaped elements distributed circumferentially around a center axis. The number of segments is preferably uneven such that the segments are not arranged directly opposite each other with respect to the center axis of the stimulator.

In an embodiment, each stimulator segment comprises five stimulator light points for illuminating the cornea of the eye, wherein three stimulator light points of each stimulator segment are arranged on a first circle with a first diameter, one stimulator light point of each stimulator segment is arranged on a second circle with a second diameter smaller than the first diameter, and one stimulator light point of each stimulator segment is arranged on a third circle with a third diameter larger than the first diameter, wherein the first circle, the second circle and the third circle are concentrically arranged about a center axis of the stimulator.

In an embodiment, all five stimulator light points of each stimulator segment may form a subset of stimulator light points, i.e. each stimulator segment forms a subset of stimulator light points. In another embodiment one or more stimulator light points of one stimulator segment may be combined with one or more stimulator lights point of other stimulator segments may form a subset. For example, the three stimulator light points arranged on the first circle of a first stimulator segment may be combined with the stimulator light point arranged on the second circle and the stimulator light point arranged on the third circle of an adjacent second stimulator segment to form a subset of five stimulator light points.

The present invention further provides a method for measuring a cornea of an eye, using an eye measuring apparatus comprising:
a stimulator comprising multiple stimulator light points for projecting a plurality of light rays onto a surface of the cornea of an eye;
a camera system for capturing reflected images of the stimulator light points;
a computational unit arranged to analyse the posterior surface of the cornea and/or to obtain a characteristic of the eye on the basis of the reflected images; and
a control unit arranged to activate selectively one or more of the multiple stimulator light points,
activating, with the control unit, subsequently different subsets of the multiple stimulator light points,
selecting, with the computational unit, for each of the different subsets of the multiple stimulator light points, at least one reflected image that corresponds with activation of the respective subset of the multiple stimulator light points, and combining, with the computational unit, the selected reflected images with each other to analyse the posterior surface of the cornea and/or to obtain the characteristic of the eye.

In an embodiment, the step of combining comprises separating, from each selected reflected image, a direct reflection area comprising a direct reflection of the one or more stimulator light points activated by the control unit, and combining the direct reflection areas of the selected reflected images into a single direct reflection image.

In an embodiment, the method further comprises the step of separating, from each selected reflected image, a background reflection area lacking a direct reflection of the one or more stimulator light points activated by the control unit, and combining the background reflection areas of the selected reflected images into a single background reflection image.

In an embodiment, each selected reflected image is split in the direct reflection area and the background reflection area.

In an embodiment, combining the background reflection areas of the selected reflected images into a single background reflection image comprises averaging the background reflection areas.

In an embodiment, combining the selected reflected images with each other comprises subtracting the single background reflection image from the single direct reflection image to obtain a background filtered single direct reflection image.

In an embodiment, the computational unit is arranged to determine on the basis of the single background reflection image a lens characteristic value representative for one or more lens characteristic of the eye.

In an embodiment, the computational unit is arranged to determine on the basis of the single background reflection image a value representative for the severity of cataract of the eye.

In an embodiment, the control unit is arranged to activate simultaneously at least one stimulator light point of each subset of the multiple stimulator light points to obtain a further reflected image, wherein the computational unit is arranged to use the further reflected image to align the selected reflected images with respect to each other.

In an embodiment, the control unit is arranged to adapt the illumination level of the one or more stimulator light points of each subsets of the multiple stimulator light points, and wherein the control unit is arranged to activate simultaneously the at least one stimulator light point of each respective subsets of the multiple stimulator light points to obtain the further reflected image with a decreased illumination level compared with an illumination level used during the activation of the one or more stimulator light points of subsequent subset of the multiple stimulator light points.

In an embodiment, the stimulator comprising two or more stimulator segments, each stimulator segment comprising one or more of the multiple stimulator light points, wherein each of the different subsets of the multiple stimulator light points is formed by the one or more of the multiple stimulator light points of one of the two or more stimulator segments.

The invention further relates to an apparatus to determine a corneal thickness of a cornea of an eye, comprising the apparatus of any of the embodiments described herein and/or wherein the apparatus is configured to carry out the method of any of the embodiments described herein. Furthermore, the invention relates to a method to determine a corneal thickness of a cornea of an eye, comprising the use of the apparatus of any of the embodiments described herein and/or comprising the steps of the method of any of the embodiments described herein.

In this apparatus and method to determine a corneal thickness of a cornea of an eye, the image of the posterior surface of the cornea may be used to analyse the cornea. The further steps to determine a corneal thickness may be carried out with the same steps as disclosed in WO 2009/127442, the contents of which are herein incorporated by reference, in its entirety.

BRIEF DESCRIPTION OF THE DRAWINGS

An embodiment of a device according to the invention will now be described in further detail, by way of example only, with reference to the accompanying drawings, in which:

FIG. 10 shows schematically the processing of the selected reflected images according to a second embodiment of the invention.

DETAILED DESCRIPTION OF THE INVENTION

Figure 1:
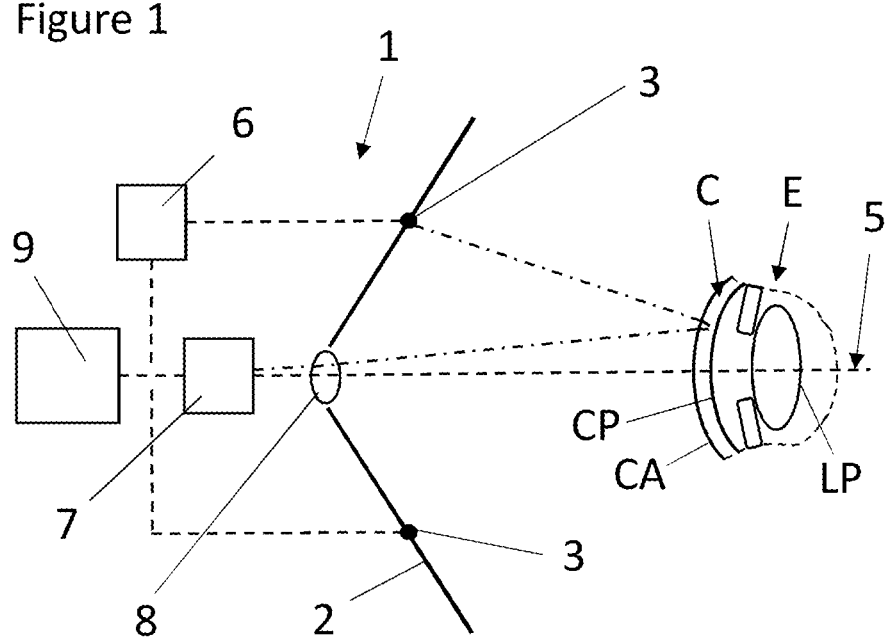
FIG. 1 shows schematically a cross section of an apparatus of the invention.

FIG. 1 schematically depicts an embodiment of an eye measuring apparatus, generally denoted by reference numeral 1. The eye measuring apparatus comprises a stimulator 2 comprising multiple stimulator light points 3. The stimulator 1 may for example have a conical shaped or a hemispherical shaped surface supporting the multiple stimulator light points 3.

Each stimulator light point 3 may have its own light source, for example a LED, but in an alternative embodiment multiple stimulator light points 3 share a light source.

Figure 2:
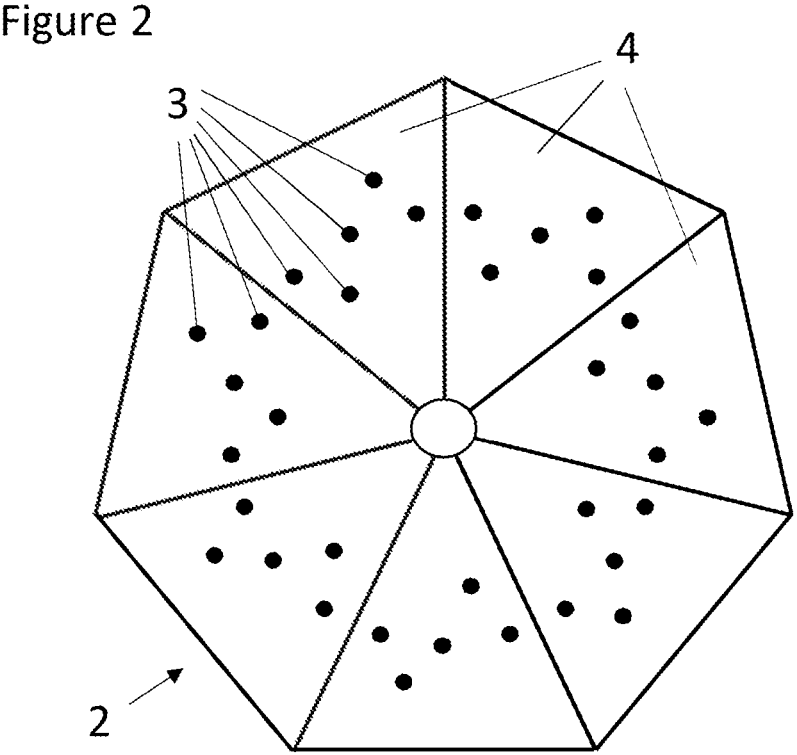
FIG. 2 shows schematically a frontal view of the stimulator of the apparatus of FIG. 1.

FIG. 2 shows a frontal view on the stimulator 2 showing the arrangement of the stimulator light points 3 in more detail. The stimulator 2 comprises seven wedge-shaped panels, each panel forming a stimulator segment 4 having five stimulator light points 3. Of these five stimulator light points 3 of each stimulator segment 4, three stimulator light points 3 are arranged on a first circle with a first diameter, one stimulator light point 3 of each stimulator segment 4 is arranged on a second circle with a second diameter smaller than the first diameter, and one stimulator light point 3 of each stimulator segment 4 is arranged on a third circle with a third diameter larger than the first diameter, wherein the first circle, the second circle and the third circle are concentrically arranged about a center axis 5 of the stimulator.

The five stimulator light points 3 of each stimulator segment 4 form a sub-set of stimulator light points that are designed to be, when desired, simultaneously activated. The subsets of stimulator light points 3 may be selectively activated.

Each of the stimulator light points 3 is arranged to illuminate, when activated, an eye E (only partly shown in cross section), in particular a cornea C of the eye E by projecting a light ray onto an anterior surface CA and/or a posterior surface CP of the cornea C of the eye E.

A control unit 6 is provided to selectively activate the subsets of stimulator light points 3. The control unit 6 may further be arranged to activate the stimulator light points 3 at different illumination levels.

The eye measuring apparatus 1 further comprises a camera system 7 for capturing reflected images of the stimulator light points, i.e. images of the eye E resulting from the light rays emitted by the stimulator light points 3 onto the anterior surface CA of the cornea C and/or the posterior surface CP of the cornea C. Some optical elements 8, such as a lens device, may be provided to focus the reflected images on a camera element, for example a CCD array, of the camera system 7.

The reflected images captured by the camera system 7 are fed into a computational unit 9 configured to process the reflected images. The reflected images are in particular processed in the computational unit 9 to analyse the posterior surface CP of the cornea C and/or to obtain a characteristic of the eye E on the basis of the reflected images.

Figure 3:
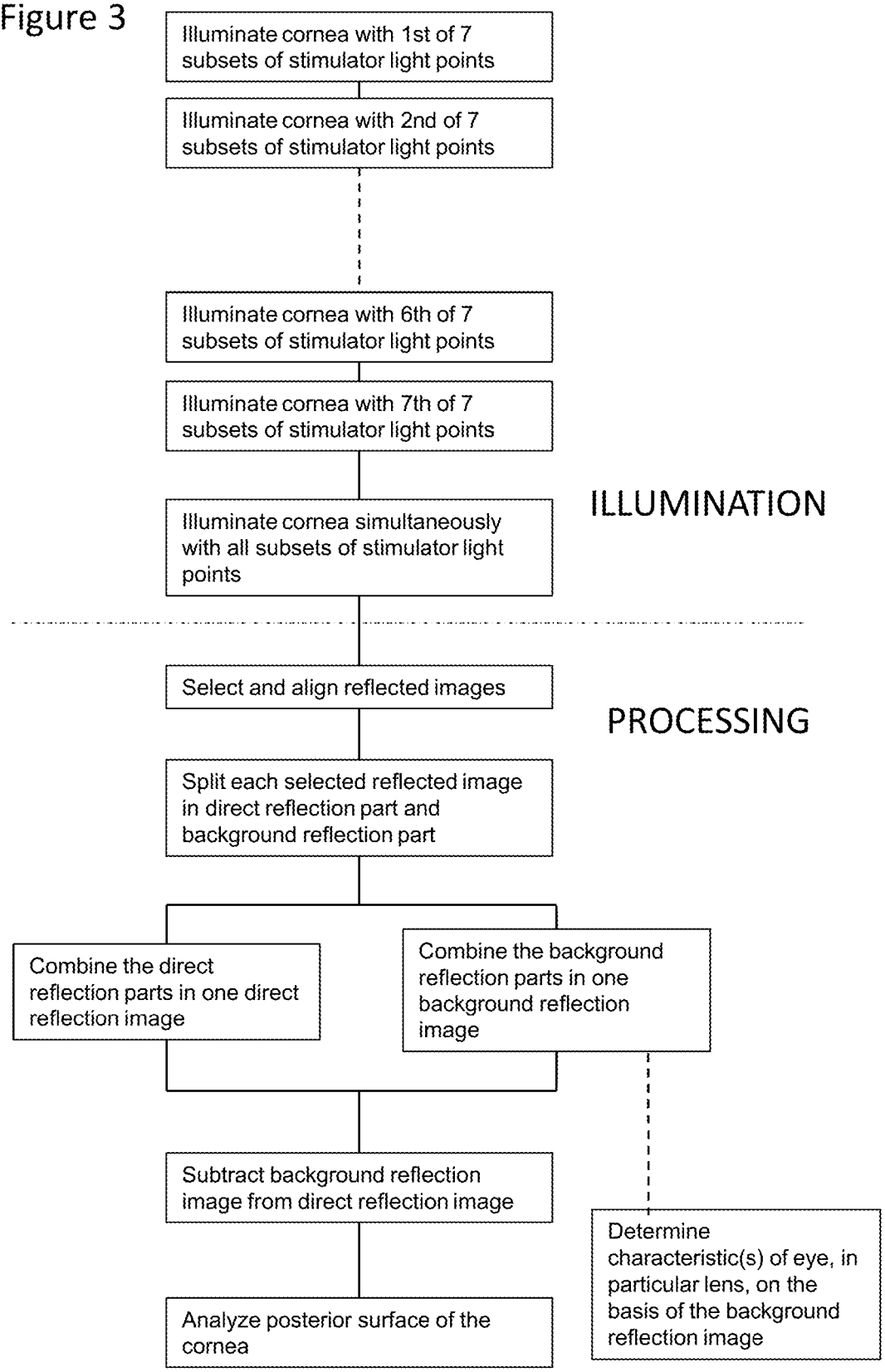
FIG. 3 shows schematically in a flow scheme the steps of illumination and processing in a method according to an embodiment of the invention.

FIG. 3 shows schematically the steps of the illumination of the cornea of the eye E and processing of the reflected images by the computational unit 9.

To obtain the reflected images of the eye E, different subsets of the stimulator light points are activated by the control unit 6 to illuminate the eye E. In the embodiment shown in FIGS. 1 and 2, the control unit 6 is configured to subsequently activate the stimulator light points of the different stimulator segments 4. Thus, first a first subset of five stimulator light points 3 is illuminated, and thereafter a second, a third, a fourth, a fifth, a sixth and a seventh subset of stimulator light points 3 are subsequently illuminated. It will be clear for the man skilled in the art that any other number of subsets of stimulator light points 3 and/or number of stimulator light points 3 within a subset, may also be used. Preferably, the subsets of stimulator light points 3 are distributed over the circumference of the stimulator, i.e. around the center axis 5, such that each subset of stimulator light points 3 is arranged within a sub-area of the complete stimulator projection area.

The order of illuminated subsets of the stimulator segments 4 of the stimulator 2 may be any order, for example following the stimulator segments 4 clockwise or anti-clockwise. However, it may be advantageous to illuminate the stimulator segments in an order wherein each subsequent illumination is performed at a stimulator segment 4 arranged at an opposite side of the stimulator 2. The advantage of this order of illumination is that movements of the eye made during the illumination phase of subsequent illumination of different subsets of stimulator light points 3 may be detected more easily by the computational unit 2 during processing of the reflected images and, consequently, can be corrected by the computational unit 2.

Figure 4:
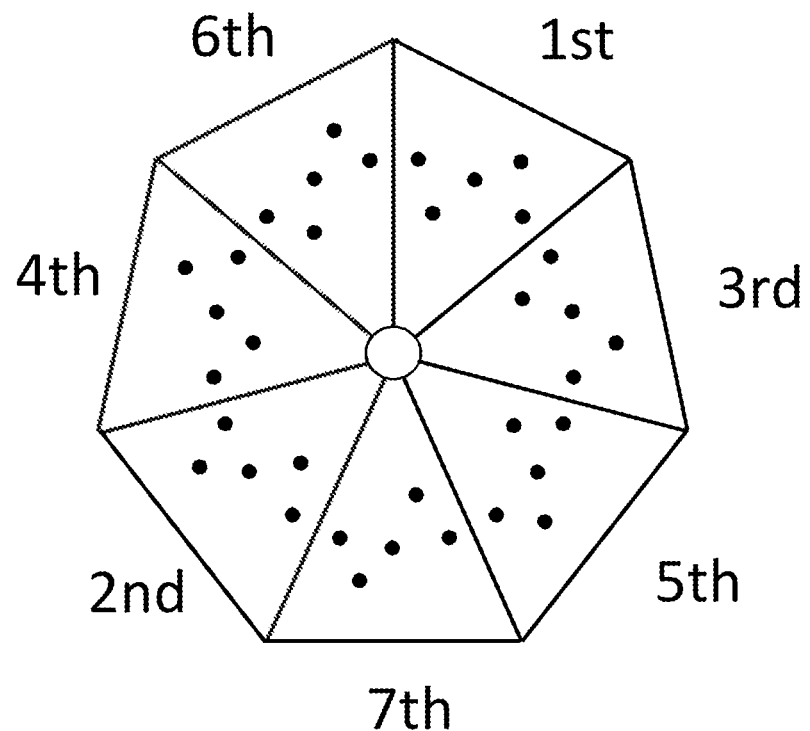
FIG. 4 indicates an order of subsequent illumination of subsets of stimulator light points.

FIG. 4 shows an example of the order of illumination in which each subsequent illumination is performed at a stimulator segment 4 arranged at an opposite side of the stimulator 2.

The camera system 7 is configured to acquire at least one reflected image of each subset of stimulator light points 3 illuminating the eye E.

Figure 5:
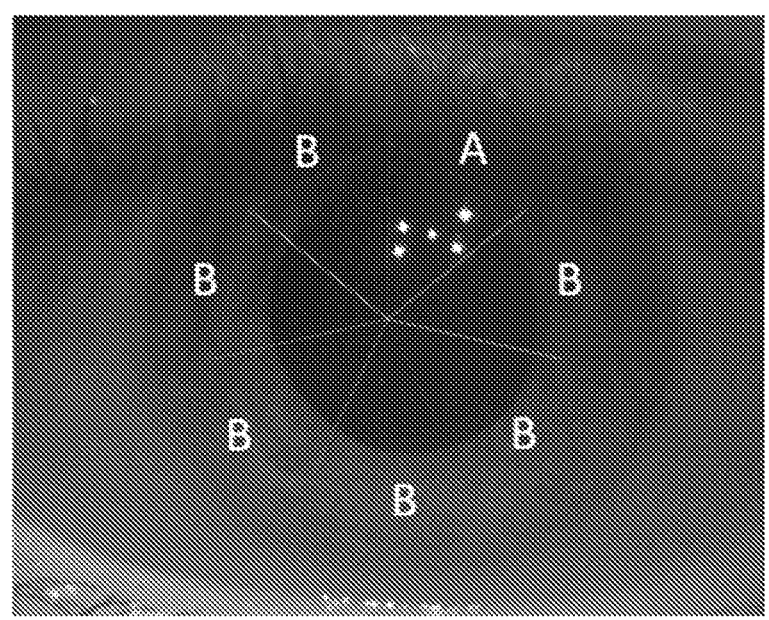
FIG. 5 shows a reflected image of illumination of one subset of stimulator light points.

FIG. 5 shows an example of a reflected image showing the direct reflections of the light rays emitted by one subset of stimulator light points 3 from the anterior surface CA and the posterior surface CP of the cornea C. The direct reflections from the anterior surface CA are relatively bright spots. The direct reflections from the posterior surface CP are more difficult to distinguish, since the direct reflections of the posterior surface CP have a substantial lower brightness, for example a factor 100 lower than the brightness of the direct reflections from the anterior surface CA.

In FIG. 5, the stimulator segments 4 are drawn on the reflected image and indicated by a letter A or B, whereby A refers to an area associated with the stimulator segment 4 which was illuminated during capturing of this reflected image and B refers to an area associated with the other stimulator segments 4.

From the reflected image shown in FIG. 5, it can be seen that a relatively low number of stimulator light points 3 is used to illuminate the eye E compared to the total number of stimulator light points 3 of the stimulator 2. As a result, the illumination level, i.e. the light intensity, of the stimulator light points 3 used may be relatively high compared to simultaneous illumination of all stimulator light points 3, without overexposure of the eye E. This high illumination level improves the visibility of the reflections of the light rays emitted by the stimulator light points 3 on the posterior surface CP of the cornea C in the reflected image.

In the embodiment of FIGS. 1 and 2, the subsets of stimulator light points 3 are non-overlapping. In order to allow aligning the reflected images with respect to each other, a further reflected image is captured by the camera system 7 when all subsets of stimulator light points 3 are simultaneously illuminated. This further reflected image provides information on the positional relationship between all stimulator light points 3 and can be used to align the reflected images with respect to each other. To avoid overexposure of the eye E during capturing of the further reflected image, the control unit 6 is configured to illuminate the stimulator light points 3 with decreased illumination level, i.e. a decreased light intensity, compared to the subsequent illumination of the subsets of stimulator light points 3.

It is remarked that the image acquired when all subsets of stimulator light points 3 are simultaneously illuminated, may be obtained before, between or after the reflected images of the different subsets of stimulator light points 3 are obtained.

In an alternative embodiment for aligning the reflected images, the subsets of stimulator light points 3 may be overlapping. For example, each subset comprises the stimulator light points 3 of two panels. By using overlapping subsets, the positional relationship between the stimulator light points 3 may be determined on the basis of the reflected images themselves. In another alternative embodiment, other characteristic features present in each of the reflected images, for example visible characteristic features of the eye E may be used to align the reflected images with respect to each other.

All reflected images captured by the camera system 6 are fed into the computational unit 6. The computational unit 6 is configured to select, for each of the different subsets of the multiple stimulator light points 3, at least one reflected image that corresponds with activation of the respective subset of the multiple stimulator light points 3. For example, the reflected image of FIG. 5 can be selected for activation of the subset of stimulator light points 3, indicated in FIG. 4 as first subset.

This step of selecting reflected images may be required since the capturing rate of the camera system 7 may not be completely synchronised with the frequency of illumination of the different subsets of stimulator light points 3. Furthermore, the illumination of the stimulator light points 3 may need some time to go from zero illumination level to the desired maximum illumination level and back to zero illumination level. In practice, the capturing rate of the camera system 7 may be substantially higher that the illumination frequency of the different subsets of stimulator light points 3. Thus, for illumination of each subset of stimulator light points 3 multiple reflected images may be obtained with different image quality. From these multiple reflected images, the computation unit 9 may select at least one reflected image that corresponds with activation of the respective subset of the multiple stimulator light points 3.

Furthermore, the computational unit 6 may be configured to align the reflected images with respect to each other using the further reflected image captured when all subsets of stimulator light points 3 are simultaneously illuminated, e.g. to correct for movements of the eye E between the acquisition of the different reflected images.

The selected images may be combined with each other to analyse the posterior surface CP of the cornea C, for example to construct a model of the posterior surface CP of the cornea C. In addition, or as an alternative, the combined selected images may be used to obtain a characteristic of the eye E.

Figure 6:
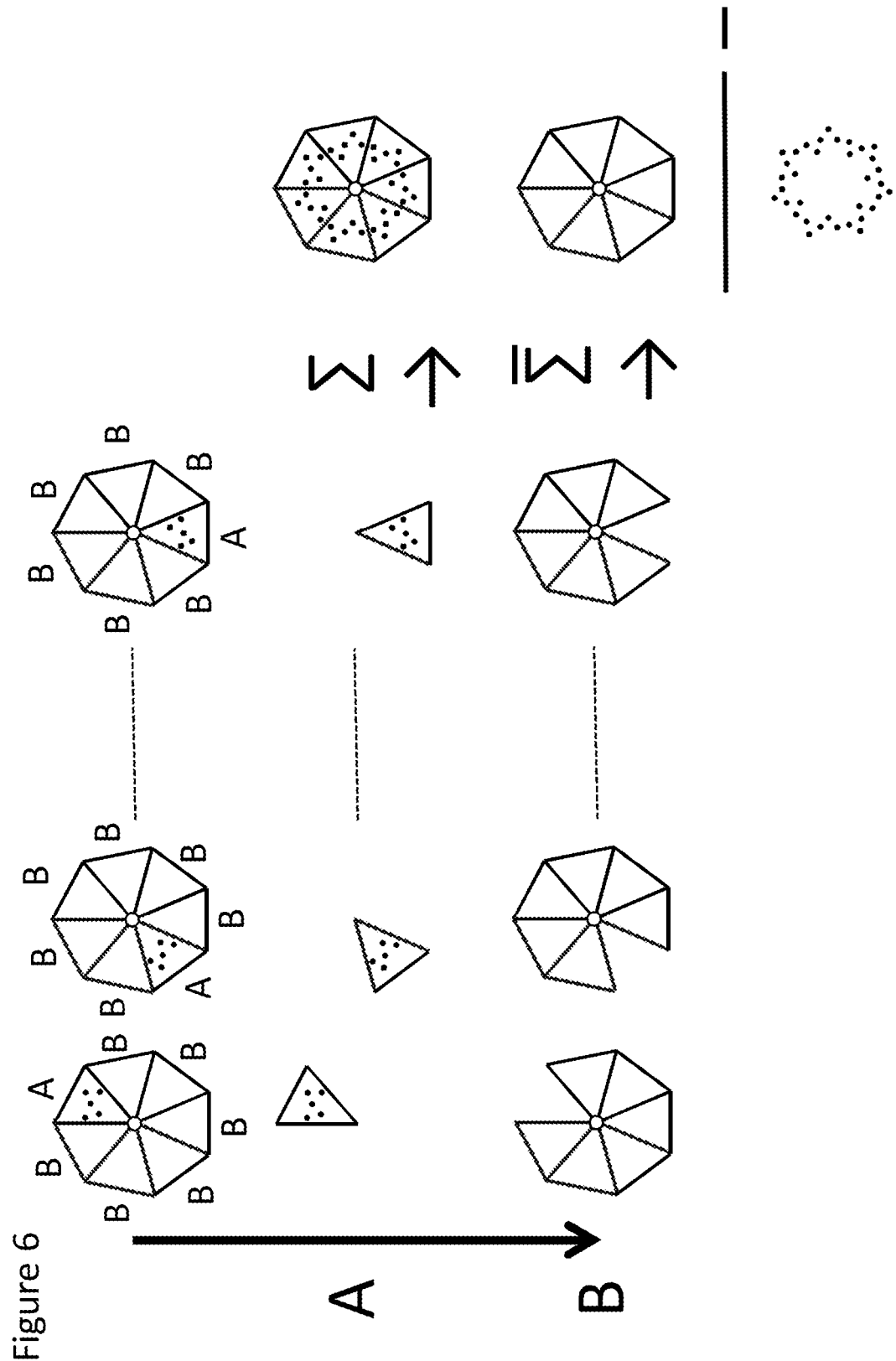
FIG. 6 shows schematically the processing of the selected reflected images according to an embodiment of the invention.

FIG. 6 shows schematically the steps that are taken to combine the selected and aligned reflected images. These steps are also indicated in the flow scheme of FIG. 3.

The top row of FIG. 6 represents the selected images. In correspondence with the indications of the stimulator segments 4 in FIG. 5, the direct reflection areas, corresponding to the illumination of a subset of stimulator light points 3 of an associated stimulator segment 4 are indicated with the letter A. All other areas of the reflected image, that contain background reflections are indicated with the letter B.

The computational unit 6 is configured to split each of the reflected images in a direct reflection area, formed by the part A of the selected reflected image, and a background reflection area, formed by the parts B of the respective selected reflected image. The separated direct reflection areas are shown in FIG. 5 in row A and the separated background reflection areas are shown in row B of FIG. 6.

In a next step, the direct reflection areas of the selected reflected images are combined to form a single direct reflection image, as shown at the right side end of row A. Since the direct reflection areas are, when properly aligned, non-overlapping, the direct reflection areas can be added to each other to form the single direct reflection image.

Figure 7:
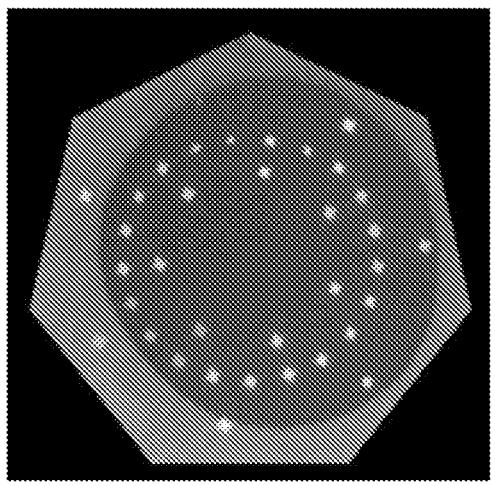
FIG. 7 shows a combined direct reflection image.

FIG. 7 shows a single direct reflection image constructed from the direct reflection areas of subsequent illumination of subsets of stimulator light points 3.

Also, the background reflection areas of the selected reflected images are combined to form a single background reflection image, as shown in FIG. 6 at the right side end of row B. These background reflection areas have a large overlap with each other of, in the above example, five sevenths of the stimulator projection area. Furthermore, the background reflection areas are not directly illuminated, but are illuminated from a particular direction. To generate a representative background image information from all stimulator light points 3, other than those directly incident on each respective part of the cornea, the background reflection areas are averaged into a single background reflection image.

Figure 8:
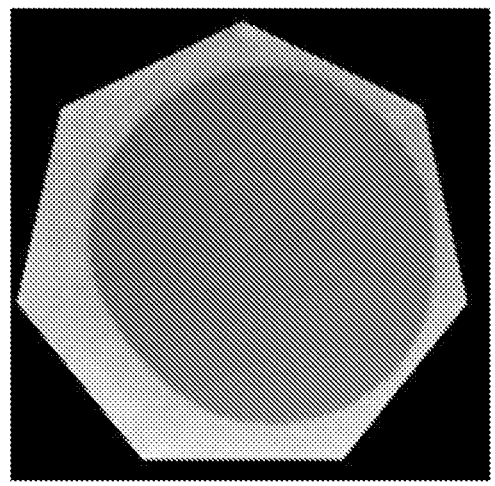
FIG. 8 shows a combined background reflection image.

FIG. 8 shows a single background reflection image constructed from averaging the background reflection areas of subsequent illumination of subsets of stimulator light points 3.

The computational unit 9 has now constructed a single direct reflection image comprising information on the direct reflections of the light rays of the stimulator light points 3 on the anterior surface CA and the posterior surface CP of the cornea C, and a single background reflection image comprising information on the background reflections, for example caused by scattering in the lens and/or reflections on the iris. Since similar background reflections are also present in the single direct reflection image, the information contained in the single direct reflection image can be improved by subtracting the single background reflection image from the single direct reflection image to obtain a background filtered single direct reflection image, as shown in the bottom right side corner of FIG. 6.

Figure 9:
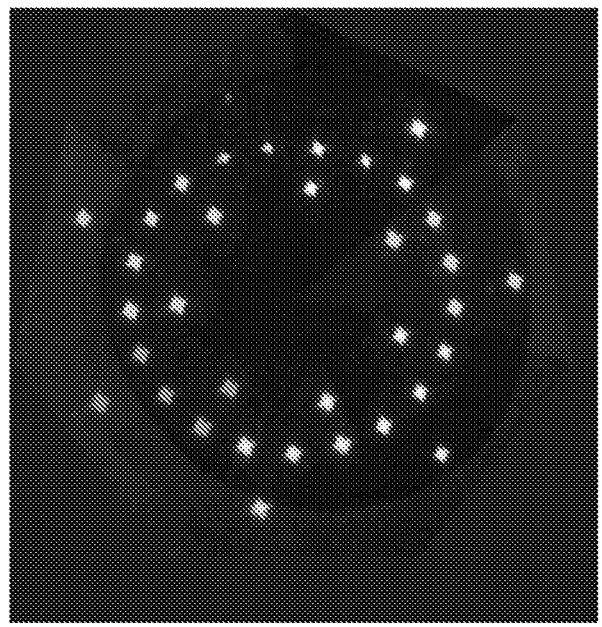
FIG. 9 shows a back ground filtered direct reflection image that results from subtracting the combined background reflection image from the combined direct reflection image.

FIG. 9 shows a background filtered single direct reflection image, that is obtained by subtracting the single background reflection image shown in FIG. 8 from the single direct reflection image shown in FIG. 7. The background filtered single direct reflection image can be used for further processing, in particular to analyse the posterior surface CP of the cornea C of the eye E. For example, the background filtered single direct reflection image may be used to determine 3D locations of the reflection points on the posterior surface CP of the cornea C, and construct, together with a mathematical model of the posterior surface CP of the cornea C, a model of the posterior surface CP of the cornea C.

In addition, or as an alternative, the single background reflection image can be used to determine one or more characteristics of the eye E, as also indicated in the process scheme of shown in FIG. 3.

The background reflections in the eye E are caused by scattering of the light rays by the tissue of the eye, like the iris, lens and other structures. Also, the background reflection image comprises direct reflections of the light rays emitted by the stimulator light points 3 from the posterior lens surface LP. Typically, these direct reflections from the posterior lens surface LP appear, with respect to a center point of the image, on the section of the reflected image diametrically opposed to the area where the direct reflections of the posterior surface CP of the cornea are found. As a result, these direct reflections are present in the background reflection images.

Indirect reflections, such as scattered light in the lens of the eye E may also be found in the single background reflection image.

On the basis of the direct and indirect reflections of the lens, the single background reflection image may be used, in itself or with other measurements, to analyse some characteristics of the lens, such as lens thickness, shape of the posterior surface of the lens, lens shape, lens tilt, decentration, etc.

It is remarked that, in case the main interest is to analyse the posterior lens surface LP, the method may be arranged to process the reflected images in such a way that the direct reflections of the posterior lens surface LP are treated as the direct reflections of interest. In such embodiment, the computational unit 9 may be configured to separate from the selected reflected images, the area of direct reflections of the posterior lens surface LP from the rest of each of the selected images, i.e. background reflection areas, in order to construct a single direct reflection image comprising direct reflections of the posterior lens surface LP. Further, the background reflection areas may be combined, by averaging, into a single background reflection image. Subtracting this single background reflection image from the single direct reflection image may provide a background filtered direct reflection image that can be used to analyse the posterior lens surface LP.

Another typical characteristic that may be analysed by the computational unit on the basis of the single background reflection image is a value representative for the severity of cataract of the eye. A substantial part of the background reflections may be caused by light scattering of the light within the lens caused by cataract in the lens. On the basis of the analysis of the single background reflection image a value relating to cataract severity of the lens may be determined. It has been found that this value may be used to predict cataract at an early stage of its development.

FIG. 10 shows an alternative embodiment of the invention, in particular an alternative embodiment of subsets of stimulator light points 3. The embodiment is based on the same stimulator 2 as shown in FIGS. 1 and 2, but in this embodiment a subset of five stimulator light points 3 is formed by the three stimulator light points 3, arranged on the first circle, of a first stimulator segment 4 in combination with a stimulator light point, arranged on the second circle, and a stimulator light point, arranged on the third circle, of an adjacent second stimulator segment 4.

Subsequent illumination of these subsets of stimulator light points 3 results in images comprising direct reflections and background reflections. The top row of FIG. 10 represents corresponding selected reflected images for each of these subsets of stimulator light points 3. The order of illumination of these subsets may be any suitable order.

Since each subset now extends over two stimulator segments, each direct reflection area also extends over two stimulator segments 4, as indicated by the letter A for each selected image. The background reflection areas of each selected reflected image are indicated with the letter B.

The computational unit 6 may now split the selected reflected images in a direct reflection area, formed by the parts A of the selected reflected image, and a background reflection area, formed by the parts B of the respective selected reflected image. The separated direct reflection areas are shown in FIG. 5 in row A and the separated background reflection areas are shown in row B of FIG. 10.

The direct reflection areas of the selected reflected images are combined to form a single direct reflection image, as shown at the right side end of row A. Correspondingly, the background reflection areas of the selected reflected images are combined to form a single background reflection image, as shown in FIG. 10 at the right side end of row B.

Finally, the single direct reflection image can be improved by subtracting the single background reflection image from the single direct reflection image to obtain a background filtered single direct reflection image, as shown in the bottom right side corner of FIG. 10.

Hereinabove, an embodiment of an eye measuring apparatus has been described having a stimulator with seven non-overlapping wedge-shaped panels, forming stimulator segments, wherein each stimulator segment comprises five stimulator light points. The stimulator light points of one or more stimulator segments may form a subset of stimulator light points to be used to selectively illuminate the eye to be measured.

In alternative embodiments, the stimulator may have any other suitable number of stimulator segments providing subsets of stimulator light points that may be overlapping or non-overlapping with other subsets of stimulator light points.

The invention claimed is:

1. An eye measuring apparatus, comprising:
    a stimulator comprising multiple stimulator light points for projecting a plurality of light rays onto a surface of the cornea of an eye;
    a camera system for capturing reflected images of the stimulator light points;
    a computational unit arranged to analyse the posterior surface of the cornea and/or to obtain a characteristic of the eye on the basis of the reflected images; and
    a control unit arranged to activate selectively one or more of the multiple stimulator light points,
wherein the control unit is arranged to activate subsequently different subsets of the multiple stimulator light points, and wherein the computational unit is arranged to carry out the following steps:
    selecting, for each of the different subsets of the multiple stimulator light points, at least one reflected image that corresponds with activation of the respective subset of the multiple stimulator light points, and
    combining the selected reflected images with each other to analyse the posterior surface of the cornea and/or to obtain the characteristic of the eye.

2. The apparatus of claim 1, wherein the step of combining comprises separating, from each selected reflected image, a direct reflection area comprising a direct reflection of the one or more stimulator light points activated by the control unit, and combining the direct reflection areas of the selected reflected images into a single direct reflection image.

3. The apparatus of claim 1, wherein the computational unit further is arranged to separate, from each selected reflected image, a background reflection area lacking a direct reflection of the one or more stimulator light points activated by the control unit, and combining the background reflection areas of the selected reflected images into a single background reflection image.

4. The apparatus of claim 3, wherein each selected reflected image is split in the direct reflection area and the background reflection area.

5. The apparatus of claim 3, wherein combining the background reflection areas of the selected reflected images into a single background reflection image comprises averaging the background reflection areas.

6. The apparatus of claim 3, wherein combining the selected reflected images with each other comprises subtracting the single background reflection image from the single direct reflection image to obtain a background filtered single direct reflection image.

7. The apparatus of claim 3, wherein the computational unit is arranged to determine on the basis of the single background reflection image a lens characteristic value representative for one or more lens characteristics of the eye.

8. The apparatus of claim 3, wherein the computational unit is arranged to determine on the basis of the single background reflection image a value representative for the severity of cataract of the eye.

9. The apparatus of claim 1, wherein the control unit is arranged to activate simultaneously at least one stimulator light point of each respective subset of the multiple stimulator light points to obtain a further reflected image, wherein the computational unit is arranged to use the further reflected image to align the selected reflected images with respect to each other.

10. The apparatus of claim 1, wherein the control unit is arranged to adapt the illumination level of the multiple stimulator light points, and wherein the control unit is arranged to activate simultaneously the at least one stimulator light point of each respective subset of the multiple stimulator light points to obtain the further reflected image with a decreased illumination level compared with an illumination level used during the subsequent activation of the subsets of the multiple stimulator light points.

11. The apparatus of claim 1, wherein the stimulator comprising two or more stimulator segments, each stimulator segment comprising at least one stimulator light point, wherein each of the different subsets of the multiple stimulator light points is formed by one or more of the multiple stimulator light points of at least one of the two or more stimulator segments.

12. The apparatus of claim 11, wherein the stimulator segments are wedge shaped elements distributed circumferentially around a center axis.

13. The apparatus of claim 11, wherein each stimulator segment comprises five stimulator light points for illuminating the cornea of the eye, wherein three stimulator light points of each stimulator segment are arranged on a first circle with a first diameter, one stimulator light point of each stimulator segment is arranged on a second circle with a second diameter smaller than the first diameter, and one stimulator light point of each stimulator segment is arranged on a third circle with a third diameter larger than the first diameter, wherein the first circle, the second circle and the third circle are concentrically arranged about a center axis of the stimulator.

14. A method for measuring a cornea of an eye, using an eye measuring apparatus comprising:
    a stimulator comprising multiple stimulator light points for projecting a plurality of light rays onto a surface of the cornea of an eye;
    a camera system for capturing reflected images of the stimulator light points;
    a computational unit arranged to analyse the posterior surface of the cornea and/or to obtain a characteristic of the eye on the basis of the reflected images; and
    a control unit arranged to activate selectively one or more of the multiple stimulator light points,
    activating, with the control unit, subsequently different subsets of the multiple stimulator light points,
    selecting, with the computational unit, for each of the different subsets of the multiple stimulator light points, at least one reflected image that corresponds with activation of the respective subset of the multiple stimulator light points, and
    combining, with the computational unit, the selected reflected images with each other to analyse the posterior surface of the cornea and/or to obtain the characteristic of the eye.

15. The method of claim 14, wherein the step of combining comprises separating, from each selected reflected image, a direct reflection area comprising a direct reflection of the one or more stimulator light points activated by the control unit, and combining the direct reflection areas of the selected reflected images into a single direct reflection image.

16. The method of claim 14, wherein the method further comprises the step of separating, from each selected reflected image, a background reflection area lacking a direct reflection of the one or more stimulator light points activated by the control unit, and combining the background reflection areas of the selected reflected images into a single background reflection image.

17. The method of claim 15, wherein each selected reflected image is split in the direct reflection area and the background reflection area.

18. The method of claim 16, wherein combining the background reflection areas of the selected reflected images into a single background reflection image comprises averaging the background reflection areas.

19. The method of claim 16, wherein combining the selected reflected images with each other comprises subtracting the single background reflection image from the single direct reflection image to obtain a background filtered single direct reflection image.

20. The method of claim 16, wherein the computational unit is arranged to determine on the basis of the single background reflection image a lens characteristic value representative for one or more lens characteristic of the eye.

21. The method of claim 16, wherein the computational unit is arranged to determine on the basis of the single background reflection image a value representative for the severity of cataract of the eye.

22. The method of claim 14, wherein the control unit is arranged to activate simultaneously at least one stimulator light point of each subset of the multiple stimulator light points to obtain a further reflected image, wherein the computational unit is arranged to use the further reflected image to align the selected reflected images with respect to each other.

23. The method of claim 22, wherein the control unit is arranged to adapt the illumination level of the one or more stimulator light points of each subsets of the multiple stimulator light points, and wherein the control unit is arranged to activate simultaneously the at least one stimulator light point of each respective subsets of the multiple stimulator light points to obtain the further reflected image with a decreased illumination level compared with an illumination level used during the activation of the one or more stimulator light points of subsequent subset of the multiple stimulator light points.

24. The method of claim 14, wherein the stimulator comprising two or more stimulator segments, each stimulator segment comprising one or more of the multiple stimulator light points, wherein each of the different subsets of the multiple stimulator light points is formed by the one or more of the multiple stimulator light points of one of the two or more stimulator segments.

* * * * *